United States Patent
Wunderlich et al.

[11] Patent Number: 6,068,854
[45] Date of Patent: May 30, 2000

[54] SOL-CONTROLLED THERMOCOLLOID MATRIX BASED ON GELATIN FOR ORAL SUSTAINED-RELEASE FORM

[75] Inventors: Jens-Christian Wunderlich, Heidelberg; Ursula Schick, Schriesheim; Jürgen Werry, Ludwigshafen; Jürgen Freidenreich, Schriesheim, all of Germany

[73] Assignee: Alfatec-Pharma GmbH, Heidelberg, Germany

[21] Appl. No.: 08/764,266

[22] Filed: Dec. 12, 1996

Related U.S. Application Data

[63] Continuation of application No. 08/244,694, filed as application No. PCT/DE92/01011, Dec. 4, 1992, abandoned.

[30] Foreign Application Priority Data

Dec. 5, 1991 [DE] Germany ............................ 41 40 192

[51] Int. Cl.[7] .................................................. A61K 9/20
[52] U.S. Cl. .......................... 424/464; 424/456; 424/469; 424/468; 424/489
[58] Field of Search ...................................... 424/464, 465, 424/489, 490

[56] References Cited

U.S. PATENT DOCUMENTS

| | | | |
|---|---|---|---|
| 4,851,392 | 7/1989 | Shaw et al. | 514/53 |
| 5,126,151 | 6/1992 | Bodor et al. | 426/99 |
| 5,330,763 | 7/1994 | Gole et al. | 424/484 |
| 5,415,871 | 5/1995 | Pankhania et al. | 424/468 |

*Primary Examiner*—Thurman K. Page
*Assistant Examiner*—William E. Benston, Jr.
*Attorney, Agent, or Firm*—Burns, Doane, Swecker & Mathis, L.L.P.

[57] ABSTRACT

A peroral depot medicament with controlled active substance release is composed of a gelatine matrix that continuously dissolves in an aqueous medium above 37° C., and a medicament distributed therein. The release of the medicament, that may be easily or scarcely soluble, lipophilic or hydrophilic, is variable in time and may be adjusted according to the medicament.

24 Claims, 1 Drawing Sheet

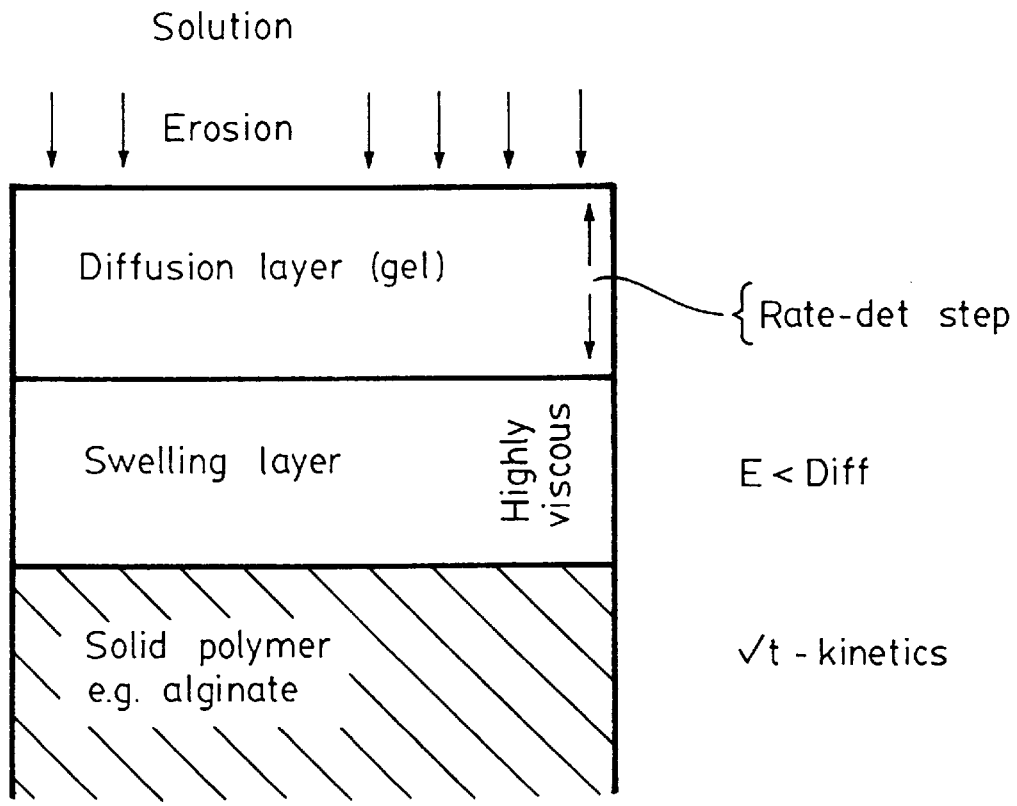
FIG._1.
(PRIOR ART)
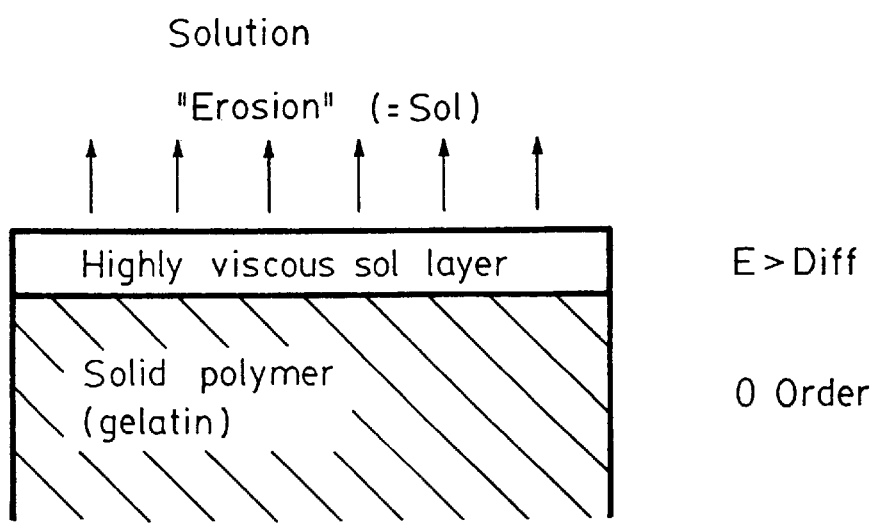
FIG._2.

SOL-CONTROLLED THERMOCOLLOID MATRIX BASED ON GELATIN FOR ORAL SUSTAINED-RELEASE FORM

This application is a continuation, of application Ser. No. 08/244,694, filed Dec. 22, 1994, now abandoned.

The present invention relates to an oral pharmaceutical form having constant release of active compound which improves in vivo medicament safety for pharmaceutical active compounds.

Sustained release of an active compound in a pharmaceutical administration form (in the narrower sense oral compositions) is desired if the biological half-life is short (as a rule 10–12 hours). As a result of long-lasting release from the pharmaceutical form, it is hoped for various advantages:

1. Improved Action

As accurate as possible an adjustment of plasma levels in the therapeutic level should on the one hand avoid plasma level variations and on the other hand side effects (under certain circumstances toxic).

2. Prolonged Action

Associated therewith is analogously a reduction in the frequency of taking with a corresponding increase in patient compliance.

With sustained-release medicaments the biopharmaceutical quality—with the parameters bioavailability and in vitro release behavior—is particularly important because, compared with single dosages, they contain relatively high doses of active compound. If the pharmaceutical control mechanism has deficiencies, activity and also tolerability can be impaired. In addition to a constant release of active compound of zero order, a pH-independent release behavior is to be ensured.

How problematic the existing prior art is should be shown with the aid of a few selected examples.

In addition to the sustained release by complexes, salts and adsorbates which is only possible in isolated cases or the alteration of the particle size or the crystal modification of the pharmaceutical substance, today essentially two principles are used for the control of active compound release:

1. The coating of active compounds/pharmaceutical forms with films and
2. matrix embedding.

In film-coating, various film-forming agents (customarily synthetic, differingly soluble or permeable polymers based on polyacrylates) are used. Liquid penetrates, for example, through pores in these membranes and causes a prolonged release of the dissolved active compound through the diffusion-inhibiting polymer barrier.

In matrix embedding, the active compound is embedded in a framework (especially of polymers and auxiliary mixtures). During gastrointestinal passage of an appropriate pharmaceutical form, the active compound is released in a more or less controlled manner or leached out of the total matrix, the remaining indigestible framework being excreted.

Owing to the complexity of the influencing quantities and process parameters, there is only incomplete success using the methods mentioned in maintaining constant plasma or tissue levels over a relatively long period of time. In addition to process-related reasons, intra- and interindividual variations, the residence period of the pharmaceutical form in the various regions of the digestive tract, food adsorption etc. often play a crucial role. Especially with poorly soluble active compounds with acid/base properties, if the sustained-release principle is unsuitable recrystallization and precipitation of the active compound in the pharmaceutical form can occur, which can cause a significant restriction of the bioavailability.

An initially very promising newer development is the so-called OROS system (oral osmotic therapeutic system), in which the active compound is intended to be released in a controlled manner through a microfine outlet opening as a result of the osmotic pressure in the interior. In addition to other disadvantages, the system can cause serious gastric irritation as far as perforations. Investigations have shown that this so-called "welding torch effect" is favored by the extremely bioadhesive properties of the administration form.

Recently, swelling polymers for hydrogel/hydrocolloid matrix tablets are increasingly under discussion as a suitable process for the controlled influencing of active compound release. It is known that e.g. alginates, cellulose derivatives of differing viscosity, and also polyacrylic acids are suitable as hydrophilic gel-forming agents. After swelling, the substances mentioned form a gel layer which can be used for sustained release.

Such a formulation based on Na alginate has been put forward for the active compound verapamil HCl, and under in vitro test conditions should have an approximately constant release of 0 order. For the preparation, however, only special alginates having specific viscosity values can be employed which moreover can only be obtained by laborious preparation. For forming the tablets, other auxiliaries of almost up to a third of the total weight are additionally required.

Although using the hydrocolloid matrix technique with the right choice of polymer in coordination with the pharmaceutical substance there can be absolute success in achieving controlled release of active compound in vitro in the isolated case, diffusion-dependent hydrocolloid systems according to more recent investigations have a linear release only at a relatively high speed of rotation in the dissolution test.

In vivo, among other things interactions of the individual polymers with the gastrointestinal fluid or the food taken can occur and uncontrollable mechanical abrasion of the swollen tablet gel layer can additionally take place as a result of gastrointestinal peristalsis.

The invention is based on the object of providing a depot medicament having a constant release of active compound, which avoids the disadvantages occurring in the prior art. In particular, an oral depot medicament for easily and poorly soluble, lipophilic and hydrophilic pharmaceutical substances is to be provided which makes possible a controllable release of the pharmaceutical substance over time and course.

This object is achieved by the oral depot medicament according to patent claim 1 and by the process for its preparation according to patent claim 18 and the use according to claim 32. Preferred embodiments of the invention are mentioned in the dependent claims.

Other International (PCT) Patent Applications of ALFATEC-Pharma GmbH, where appropriate also the PAZ Arzneimittelentwicklungsgesellschaft mbH, of the same date relate to the pharmaceutical administration of nanosols and their preparation (81AL2730 corresponding to German Patent Application P 41 40 195.6), the immediate-effect form of 2-arylpropionic acid derivatives (81AL2731 corresponding to German Patent Application P 41 40 185.9), the sustained-release form of dihydropyridine derivatives (81AL2732 corresponding to German Patent Application P 41 40 194.8), the immediate-effect form of S- and R-ibuprofen (81AL2733 corresponding to German Patent Application P 41 40 179.4), the sustained-release form of S- and R-ibuprofen (81AL2734 corresponding to German Patent Application P 41 40 172.7), the immediateeffect form of S- and R-flurbiprofen (81AL2735 corresponding to German Patent Application P 41 40 184.0), the sustained-release form of S- and R-flurbiprofen (81AL2736 corresponding to German Patent Application P 41 40 183.2), the sustained-release form of 3-indolylacetic acid derivatives (81AL2737 corresponding to German Patent Application P 41 40 191.3) or the oral administration of peptide pharmaceutical substances (81AL2738 corresponding to German Patent Application P 41 40 186.7). Their disclosure is also made the subject of the disclosure of the present patent application.

According to the invention, an oral depot medicament based on gelatin is provided which has a sol-controlled linear liberation of a pharmaceutical substance which takes place independent of pH and without uncontrolled erosion or abrasion. The pharmaceutical substance is present in the proposed matrix protected from penetrating gastrointestinal fluid and goes directly into solution without prior diffusion from the sol form of the polymer.

The controlled release can thus be varied in terms of time using the medicament depot form according to the invention and reproducibly adjusted very precisely with high batch conformity.

The invention additionally increases medicament safety and shelf life. For pharmaceutical substances with problematic bioavailability or for pharmaceutical substances which are still not orally available, novel solutions are shown.

The mechanism of pharmaceutical substance liberation occurring according to the invention in relation to the prior art is illustrated schematically in FIGS. 1 and 2.

FIG. 1 schematically shows the release of the pharmaceutical substance embedded in a solid polymer, e.g. alginate, under physiological conditions according to the prior art. The solid polymer, e.g. alginate, in aqueous medium forms two layers which consist of a highly viscous swelling layer and the diffusion layer (gel). In addition to erosion, diffusion-dependent pharmaceutical substance liberation takes place simultaneously in the gastrointestinal tract. The release of the pharmaceutical substance thus corresponds in terms of time to a $\sqrt{t}$ law, in which the erosion is smaller than the diffusion rate (E<Diff) of the pharmaceutical substance. As the diffusion is the rate-determining step, a controlled release is additionally dependent both on the swelling layer and the erosion. The gelatinous diffusion layer and viscous swelling layer are moreover mechanically unstable.

FIG. 2 schematically shows the release of the pharmaceutical substance according to the present invention. The solid polymer, the gelatin, in which the pharmaceutical substance is embedded, under identical conditions forms a highly viscous sol layer which only possesses low thickness. The liberation of pharmaceutical substance takes place exclusively by continuous dissolution of this layer (E>Diff), which builds up continuously with the same layer thickness. The pharmaceutical substance is released constantly according to zero order in this process and is not dependent on additional influencing factors. An advance diffusion process is unnecessary and the mechanical stability is guaranteed.

Gelatin is a known pharmaceutical auxiliary which has a marked thermoreversible sol/gel formation behavior depending on the molecular composition. There has only recently been success by the use of HPLC and other methods in elucidating the molecular fine structures and defining the properties and the behavior of the various molecular weight fractions. This fact makes it possible today to bring into use for the various application purposes standardized grades which open up novel technological areas to the natural biopolymer gelatin.

It is possible for the first time using the present invention to propose a sustained-release matrix tablet based on gelatin reproducibly and with novel properties, which leads to a distinct improvement in the prior art and medicament safety. Furthermore, special types of gelatin are employed according to the invention which, inter alia, are particularly low in peptide and exhibit narrow molecular weight distributions. Gelatin derivatives and fractionated gelatins may also be suitable.

Special gelatin preparation processes and their properties can be taken from the abovementioned patent applications of the same date.

A sustained-release form described in the object of the invention is already obtained by classifying a commercially available gelatin ground into very fine grains (bloom value 220, maximum of the molecular weight distribution at 100 kD) and a pharmaceutical substance to a grain size of 70 μm, preparing a powder mixture of pharmaceutical substance, gelatin powder and customary tabletting auxiliaries and pressing directly, to give the tablet, with a defined residual moisture content.

Surprisingly, it has been shown that all gelatins which have a maximum in the molecular weight distribution in the range from $10^4$ to $10^7$ D are suitable to release the pharmaceutical substance linearly over several hours in aqueous medium at 37° C. in a sustained manner. This fact is all the more surprising as hard gelatin capsules, as is known, dissolve completely in a few minutes under identical test conditions.

Investigations on the hydrocolloid matrix tablets mentioned in the prior art show that a plurality of phenomena occur in active compound release of polymer-containing pharmaceutical forms. Thus a clear statement about the rate-determining step of pharmaceutical substance liberation is significantly restricted by the following processes partly taking place simultaneously:

penetration of water into the surface formation of a gel layer dissolving of the active compound diffusion of the active compound through the gel layer erosion of the gelatinous matrix simultaneous release of the active compound and dissolution of the polymer.

The sol-controlled thermocolloid matrix tablet according to the invention leads in contrast to this for the first time to a tablet which reduces the above-mentioned phenomena to a minimum. Thus the liberation of pharmaceutical substance in the course of time depends only on the almost invisible sol layer on the surface, whose dissolution is the rate-determining step. This layer is moreover interestingly able effectively to prevent a deeper penetration of water and thus a swelling of the matrix. The tablet, which is non-swelling and stable in aqueous medium, is therefore also insensitive in vivo to mechanical effects or abrasion.

Fundamentally, all commercially available types of gelatin which above 37° C. no longer possess gel formation power and are pressed in a grain size below 200 μm, preferably below 50 μm, are suitable. The weight ratio of pharmaceutical substance to gelatin should not be over 1:1, it being possible to increase this ratio to 1:0.5 and more by means of special gelatin which is particularly low in peptides and highly viscous.

In a more extensive embodiment of the basic thinking according to the invention, the pharmaceutical substance, calculated on the tablet dosage, is homogeneously incorporated in dissolved, suspended or emulsified form into an aqueous gelatin sol or one mixed with organic solvents. In contrast to most natural and synthetic hydrocolloids, gelatin solutions are in comparison of rather low viscosity even at relatively high concentrations. Advantageously, the solvent of the above gelatin/pharmaceutical substance mixture can therefore be removed without problems and gently by spray-drying.

Technologically, pharmaceutical substance/gelatin powder prepared according to the invention can be pressed with or without prior granulation to give tablets or pellets which are distinguished by high breaking strength and low friability. When using the spray-drying technique with subsequent direct tabletting, the optimum grain size range for achieving a readily pourable and highly pressable powder is below 200 μm, preferably below 50 μm.

If required, other auxiliaries, polymers of synthetic or natural origin or viscosity-enhancing substances can be added to the composition based on gelatin according to the invention if the sol-controlled release is not restricted.

The tablets or pellets according to the invention can be provided e.g. with enteric-resistant film-forming agents and other pharmaceutically known coatings.

Moreover, coated tablets can also be prepared according to the invention for protection and for control of the release of enzymatically sensitive pharmaceutical substances.

The proposed procedure can significantly expand the width of application of the sustained-release form put forward. The biopolymer gelatin, in contrast to other pharmaceutically employable macromolecules, furthermore possesses other interesting properties which are additionally utilized according to the invention:

molecular weight fraction-dependent behavior amphiphilic properties and good surf actant formation power pH-variable charge states controllable and temperature-dependent sol/gel formation.

Thus e.g. even without further use of emulsifiers, using a single auxiliary emulsions can be prepared in spray-dried form which are suitable for direct tabletting. Liquid lipophilic pharmaceutical substances can thus also be processed in a surprisingly simple manner to give a sustained-release pharmaceutical form.

Suitable pharmaceutical substances which can be employed according to the invention are all pharmaceutical substances which do not have any incompatibility with gelatin. Liquid and pasty or oily solids and also easily and poorly soluble solids can thus be employed.

Furthermore, imperfect taste can be effectively prevented by the process and easily volatile substances protected from change.

In addition to the protection of the pharmaceutical substance from oxidation and hydrolysis and thus an increase in the shelf life which can be achieved by spray embedding, technological advantages are also obtained. The homogeneity and the very good direct tabletting properties of the powder obtained lead to a simplification of the preparation process and improve the batch conformity.

According to the invention, suitable pharmaceutical substances can be the following:

from the analgesics/antirheumatics group, e.g.:
  idometacin, acemetacin
  ibuprofen, flurbiprofen, ketoprofen
  diclofenac
  acetylsalicylic acid from the alkaloids group, e.g.:
  codeine
  dihydrocodeine from the xanthine derivatives group, e.g.:
  theophylline, diprophylline from the beta-blockers group, e.g.
  pindolol
  propranolol
  metoprolol
  oxprenolol from the antihypertensives group, e.g.:
  etilefrin, renin antagonists from the Ca antagonists group, e.g.:
  nifedipine and structural relatives
  diltiazem
  verapamil from the antiarrythmics group, e.g.:
  procainamide
  prajmaline
  disopyramide from the antitussives group, e.g.:
  oxeladine citrate
  dextromethorphan from the circulation-promoting agents group, e.g.:
  vincamine from the mucolytics, broncholytics and antiasthmatics group, e.g.:
  ambroxol, salbutamol from the vasodilators group, e.g.:
  dihydroergotoxin from the coronary therapeutics group, e.g.:
  molsidomine, nitric acid esters (isosorbide mono- and dinitrates)

from the psychotherapeutic agents group, e.g.:
  oxazepam from the antihistamines group, e.g.:
  carbinoxamine from the vitamins group, e.g.:
  fat- and water-soluble vitamins from the diuretics group, e.g.:
  furosemide from the hypolipidemic pharmaceutical substances group, e.g.:
  bezafibrate, fenofibrate, xantinol nicotinate from the group of pharmaceutical substances for the treatment of acquired immunodeficiency AIDS, e.g. renin antagonists from the antibiotics/chemotherapeutics group, e.g.:
  nitrofurantoin from the peptide pharmaceutical substances group, e.g.:
  insulin, interferons, renin antagonists.

As already presented in detail in the patent applications mentioned at the beginning, differences in absorption can be advantageously equalized and tolerability increased using the procedures according to the invention.

Higher-dose pharmaceutical substances are furthermore particularly suitable, such as e.g. painkillers from the non-steroidal antirheumatics (NSAR) group and their enantiomers.

Furthermore, it has interestingly been shown that the sustained-release period can be varied within wide limits as a direct function of the type of gelatin selected. Cold-watersoluble gelatins which possess a molecular weight of below $10^4$ D are rather unsuitable for sustained release. A sustained release of 1–2 hours can be set by low-bloom or low viscosity gelatin. Medium to high-bloom or medium to high viscosity types, according to their molecular weight distribution, linearly prolong the period of complete pharmaceutical substance liberation to up to 16 hours and more.

The development and the scaling-up of a sustained-release form which has a desired release period for the corresponding pharmaceutical substance, can be standardized and made reproducible by a further proposal according to the invention. If e.g. a dissolution of the pharmaceutical substance in aqueous gelatin solution with subsequent spray embedding is selected as a suitable procedure, from a critical pharmaceutical substance/gelatin ratio this loading can lead to a change in the physicochemical properties of the gelatin employed. Thus a type of gelatin suitable per se with a sustained-release power of, for example, 10 h can have a correspondingly shorter release period as a result of the "salting-out effect" at high dosage of the active compound.

In order to make these phenomena in the preformulation quantitatively measureable, it is possible according to the invention to proceed as follows.

By differential thermal analysis and measurement of the molecular weight distribution (HPLC), a statement can be made, to start with, about which type of gelatin is suitable for the corresponding application. The bloom number of the selected types of gelatin (gelatin mono-graph, bloom test according to German Pharmacopeia 9) is determined. Under identical test conditions and concentration ratios, a second measurement is carried out in which the pharmaceutical substance is present dissolved in gelatin in the precalculated concentration. A difference from the starting bloom value results here. The measured reduction in the bloom value between the first and second measurement is used as a direct measure of the interaction of the dissolved pharmaceutical substance with gelatin.

If the starting gelatin, for example, has a bloom value of 250 and the second measurement with pharmaceutical-substance-loaded gelatin leads to a bloom value of e.g. 220, by use of a 270 bloom gelatin the originally desired release characteristics corresponding to the table (dissolution times) from Example 1 can be set again.

An analogous process can be illustrated by comparative measurement of the viscosity, which in particular allows a statement about the viscosity-determining gelatin molar fraction above $10^6$ D.

The sol-controlled thermocolloid matrix according to the invention can furthermore offer novel solutions for poorly soluble pharmaceutical substances with problematic bioavailability, which results from matrix embedding in the nanosol technique of the patent applications mentioned at the beginning, in particular "Pharmazeutisch applizierbares Nanosol and Verfahren zu seiner Herstellung", (Pharmaceutically administerable nanosol and process for its preparation), "Ein 2-Aryl-propion-saäurederivat in Nanosolform enthaltendes Arzneimittel und seine Herstellung", (Medicament containing a 2-aryl-propionic acid derivative in nanosol form and its preparation), "Ein Dihydropyridin-derivat in Nanosolform enthaltendes Arzneimittel und seine Herstellung", (Medicament containing a dihydropyridine derivative in nanosol form and its preparation) and "Perorale Applikationsform fur Peptidarzneistoffe", (Oral administration form for peptide pharmaceutical substances). The poorly soluble pharmaceutical substance which is present and stabilized in nanosol form is pressed after drying, preferably spray-drying, to give the corresponding tablets. In addition to the charge state of the gelatin/pharmaceutical substance nanosol which is to be taken into account, within the meaning of the present invention types of gelatin are selected which, according to preliminary test, have the desired sustained-release potential. In addition to the properties of the matrix according to the invention already described, the advantage of the process also lies in the protection of the nanosol pharmaceutical substance from degradation and premature instability as a result of gastrointestinal fluid penetrating into the tablets, such as can occur e.g. in swelling hydrogel matrices.

In particular, the release of poorly soluble pharmaceutical substances with marked acid/base properties can thus be reliably sustained with improvement of absorption.

Further protection from premature degradation of a sensitive pharmaceutical substance can also be achieved by microencapsulation using two differently charged types of gelatin. In this case the invention proposes the following process:

The pharmaceutical substance is first coacervated by solvent evaporation of a mixture of type A and type B gelatins. Further processing takes place according to the invention by means of direct spray-drying of the mixture obtained without prior separation of the microcapsules. The powder obtained can be processed in tablet form to give a sol-controlled thermocolloid matrix due to the non-separated and non-coacervated gelatin fraction. For this special case of the invention types of gelatin are preferably suitable which have a part of the molar fraction above 300 kD of at least 20%. Such types of gelatin, in particular of acidically worked-up gelatin (type A) can only be obtained by special preparation processes and are distinguished by a low peptide content. A particularly homogeneous distribution of the microcapsules obtained can be obtained by use of type A and B gelatins with identical or similar molecular weight distribution.

A pharmaceutical form prepared in this way releases the active compound protected in mainly microencapsulated form and continuously and can thus be advantageously used orally for pharmaceutical substances which are subjected to enzymatic degradation in the GIT, such as e.g. peptide pharmaceutical substances. The extremely high viscosity of the types of gelatin employed additionally facilitates the desired concentration on the mucosa or epitheleal layer during gastrointestinal passage.

It is known that a so-called pulsed release in tablet form can be obtained by means of alternately active-compound-containing and active-compound-free layers, e.g. with hydrocolloid matrices.

The width of variation of the invention will be demonstrated by an appropriate pharmaceutical form. In this case the already-mentioned non-swelling and stable tablet surface in aqueous medium, which does not lead to any uncontrollable erosion, acts advantageously on the time-dependent dosage form. The active-compound-containing and active-compound-free layers can thus be composed e.g. as follows:

Active-compound-containing layers are built up from linearly releasing, sol-controlled matrices according to the invention which, by selection of a suitable type of gelatin, release the active compound e.g. in one hour. Layers without active compound, if the pulsed release is desired at shorter intervals, can be built up on the basis of a gelatin of low molecular weight composition.

In this manner, stable, non-swellable tablets with three- to fourfold pulsed release can be prepared. If a multiply-pulsed sustained release over a longer period is desired, the decrease in the layer thickness compulsorily associated therewith (due to the maximum tolerable tablet size) of the active-compound-containing and active-compound-free zones can be compensated or controlled in a time-dependent manner by selection of types of gelatin with higher molecular weight composition or viscosity. In the extreme case, very thin, time-delayed and constantly dissolving active-compound-free layers can be built up for pulsed control, which consist of special types of gelatin with sol-formation temperatures of just under 37° C.

In this manner, in spite of multiple pulsing a stable tablet with a low web height can be prepared.

In an analogous manner, such a tablet can also be built up using two different pharmaceutical substances without active-compound-free layers. Thus e.g. in rheumatic therapy a combination of S- and R-flurbiprofen or other nonsteroidal antirheumatics which possess a high active compound potential can be built up alternately with the painkilling (rapid influx) and the anti-inflammatory (prolonged influx) component.

In order to ensure a high batch conformity with this complicated, but up to date pharmaceutical form and to guarantee a controlled construction of the layers, the active compound should preferably be incorporated in spray-dried form.

Depending on the gelatin preparation procedure (extent of degradation of native collagen and acidic or alkaline hydrolysis process), gelatin of Type A or Type B has a characteristic molecular weight spectrum or molecular weight distribution. Table 1 indicates the molecular weight distributions of various types of gelatin or of collagen hydrolyzates, and the percentage content (frequency) of individual -molecular weight ranges.

The predominance of an individual range compared with the other molecular weight ranges of the same gelatin can be seen clearly in the individual columns. This range is thus the maximum of the molecular weight distribution (it is 95 kD e.g. for the Type B gelatin shown in the Figure). The concept of the "maximum in the molecular weight distribution", however, is to be separated strictly from the concept of the "average mean molecular weight". This mean value is 165 kD for the gelatin of the Type B mentioned.

In the formulation of medicaments, the pharmacist makes a fundamental distinction between:

1. pharmaceutical preparation, i.e. of a release of the pharmaceutical substance, e.g. from a tablet in a manner which is rapid (immediate-effect form) or prolonged (sustained-release form) timewise; and
2. the pharmaceutical-substance-specific absorption site, such as e.g. the stomach or specific sections of the intestine.

The nanosols according to the invention are able, independently of the pharmaceutical preparation, to be absorbed in the entire gastrointestinal region on account of their special composition. They can therefore be advantageously processed to give immediate-effect or sustained-release pharmaceutical forms.

Pharmaceutical substances having problematic or restricted bioavailability can be used advantageously for pulsed release by means of the embodiments such as e.g. nanosol technique indicated in the descriptive part of the invention.

The following examples are intended to illustrate the invention in greater detail:

EXAMPLE 1

Types of gelatin having bloom values of 50, 150, 200, 250, 300 and 350 are concentrated or spray-dried in the customary manner at 50° C. in concentrations of 5–10%. The powder is granulated and directly pressed with a residual moisture of 12% on an eccentric press with addition of FST complex to give tablets having a weight of 400 mg. According to USP XXI (paddle apparatus), the average dissolution times of 6 tablets in each case in 900 ml of water are determined at 100 rpm and 37° C. The dissolution times found can be taken from the table. Similar dissolution times are obtained with tablets of very finely ground gelatin powder (grain size below 200 µm) of the abovementioned grades.

TABLE 1

Molecular weight distribution of various known types of gelatin or of known collagen hydrolyzates

| Molecular Mass Distribution (kD) | Native Collagen % | Gelatin Type B % | Gelatin Type A % | Collagen hydrolyzate Gelita ® Collagel A | Collagen hydrolyzate Gelita ® Collagel B | Collagen hydrolyzate Gelita ® Sol C | Elastin hydrolyzate Gelita ® Gelastin |
|---|---|---|---|---|---|---|---|
| >360 | 100 | 18.0 | 18.0 | 0 | 0 | 0 | 0 |
| 285 | 0 | 7.0 | 9.0 | 0 | 0 | 0 | 0 |
| 145–237 | 0 | 20.0 | 34.0 | 1.0 | 1.5 | 0 | 0 |
| 95 | 0 | 26.0 | 11.0 | 0 | 0 | 0 | 0 |
| 95–50 | 0 | 16.3 | 13.4 | 2.6 | 4.0 | 1.1 | 0 |
| 50–20 | 0 | 7.4 | 9.1 | 18.0 | 14.5 | 0.3 | 0 |
| 20–10 | 0 | 3.9 | 3.8 | 43.0 | 31.5 | 3.7 | 0.2 |
| 10–5 | 0 | 3.0 | 3.0 | 15.4 | 20.0 | 12.2 | 5.2 |
| 5–2 | 0 | 0 | 0 | 6.0 | 14.0 | 26.0 | 93.9 |
| 2–1 | 0 | 0 | 0 | 7.0 | 8.0 | 23.0 | 0 |
| <1 | 0 | 0 | 0 | 6.5 | 7.0 | 34.0 | 0 |
| MW | 360 | 165 | 185 | 12–18 | 12–18 | 3 | 2–3 |

Table of dissolution times:

| Bloom value (g) | Dissolution times (min) |
|---|---|
| 50 | 55 |
| 150 | 120 |
| 200 | 178 |
| 250 | 265 |
| 300 | 413 |
| 350 | 627 |

EXAMPLE 2

500 g of gelatin having a bloom value of 300 are dissolved in 10 l of water at 50° C. 10 g of Methylene Blue are then dissolved in the sol, the solution is concentrated and spray-dried and the residue is pressed analogously to Example 1 to give 300 mg tablets. In a release apparatus (paddle) according to USP XXI, the release of the colorant from in each case 6 of the 300 mg tablets is determined under the following conditions: 900 ml of water, 50 rpm, 37° C. 1 ml of sample solution in each case is taken at specific times and the content of Methylene Blue released is determined at 663 nm by VIS spectroscopy. The values obtained can be taken from the table.

Release table:

| Time [h] | Release in % |
|---|---|
| 0.25 | 8 |
| 0.5 | 13 |
| 1 | 22 |
| 1.5 | 33 |
| 2 | 42 |
| 3 | 58 |
| 4 | 67 |
| 5 | 83 |
| 6 | 98 |

Tablets prepared and measured under identical conditions containing gelatin of characteristic bloom number 330 show a 100% release after 485 min.

Compared with Example 1, the tablet batches described show a shorter dissolution time which in this case is dependent on the lower tablet weight.

EXAMPLE 3

As verapamil HCl is a water-soluble salt, the preliminary test for bloom depression is carried out as follows:

A gelatin according to Example 1 with a dissolution time of 413 minutes shows a value of 300 bloom by the bloom test according to German Pharmacopeia 9 (7.5 g of gelatin in 105 ml of water). In a second experiment, 2.37 g of verapamil HCl are added to an identically concentrated gelatin solution, dissolved therein and the test is carried out again according to the procedure. A value of 280 bloom is determined. In order to compensate for the reduction in the gel strength and to obtain the desired dissolution time, a gelatin of 315 bloom is employed.

0.12 kg of verapamil HCl are stirred into a gelatin solution prepared from 0.38 kg of the gelatin specified above and 8 l of water at 50° C. The clear solution obtained is spray-dried and pressed with a mean particle size of 50–60 µm with addition of FST complex in an—eccentric press to give tablets with a dosage of 120 mg and 500 mg total weight.

The dissolution test (paddle) at 37° C., 900 ml of water and 50 rpm with a change in the test medium from artificial gastric juice to artificial intestinal juice after 2 hours on average shows the following pH-indepen-dent release data:

| Time (h) | Release in % |
|---|---|
| 1 | 24 |
| 2 | 34 |
| 3 | 56 |
| 4 | 65 |
| 5 | 82 |
| 6 | 95 |
| 7 | 100 |

EXAMPLE 4

Propranolol HCl tablets with a tablet weight of 500 mg and a dosage of 80 mg are to be prepared. The gelatin grade employed is 290 bloom, which results from the desired sustained-release period (see Example 1) and analogously to the preliminary test (Bloom compensation, see Example 3).

80 g of propranolol HCR are dissolved in 0.42 kg of gelatin of the above grade and 5 l of water at 50° C. The tablet batch is then prepared as described in Example 3.

The dissolution test according to USP XXI (rotating basket) in 1000 ml of dilute HCl, 37° C. and 100 rpm shows the following average values:

| Time (h) | Release in % |
|---|---|
| 1 | 16 |
| 2 | 39 |
| 3 | 52 |
| 4 | 73 |
| 5 | 91 |
| 6 | 100 |

What is claimed is:

1. A sustained release medicament, comprising a tablet which releases medicaments in an approximately constant manner per time interval in aqueous medium above 37° C., consisting of a matrix of gelatin or fractionated gelatin or mixtures thereof and a lipophilic and/or poorly water soluble pharmaceutical substance dispersed therein, wherein the pharmaceutical substance is present in emulsified, disperse, or colloidal disperse form with a particle size below 200 µm.

2. A sustained release medicament as in claim 1, wherein the gelatin, fractionated gelatin and/or mixture thereof have a maximum in the molecular weight distribution which is in the range from $10^4$ to $10^7$ D.

3. A sustained release medicament as in claim 1, wherein the gelatin has characteristic numbers of 50 to 400 bloom.

4. A sustained release medicamenit as in claim 1, wherein the matrix is a tablet which consists essentially of gelatin or fractionated gelatin and further containing synthetic or natural polymers and other auxiliaries.

5. A sustained release medicament as in claim 1, wherein the pharmaceutical substance is present in emulsified form.

6. A sustained release medicament as in of claim 1, wherein the pharmaceutical substance is present in disperse form with a particle size of 2 to 200 µm.

7. A sustained release medicament as in claim 1, wherein the pharmaceutical substance is present in molecularly disperse to colloidal disperse form.

8. A sustained release medicament as in claim 1, wherein one or more pharmaceutical-substance-containing layer(s) alternate in the medicament with one or more pharmaceutical-substance-free layer(s).

9. A sustained release medicament as in claim 1, wherein said tablet comprises alternating layers of said matrix wherein adjacent layers contain different pharmaceutical substances.

10. A sustained release medicament as in claim 1, which is provided with a coating of a synthetic or natural polymer.

11. A sustained release medicament as in claim 1, which is present in an immediate release form.

12. A process for the production of a sustained release medicament as in claim 1, which comprises preparing a powdered gelatin pharmaceutical substance mixture using a gelatin and/or fractionated gelatin which dissolves slowly in the aqueous medium above 37° C. and compressing the mixture.

13. The process as in claim 12, wherein the gelatin/pharmaceutical substance mixture is essentially prepared from gelatin and/or fractionated gelatin in addition to synthetic and/or natural polymers and other auxiliaries as well as the pharmaceutical substance.

14. The process as in either claim 12 or 13, wherein the mixture is prepared by homogeneously mixing powdered gelatin and powdered pharmaceutical substance.

15. A process for the production of a sustained release medicament as in claim 1, which comprises compressing the gelatin/pharmaceutical substance mixture directly to form a tablet.

16. The process as in claim 12, wherein the gelatin pharmaceutical substance mixture is granulated before compressing.

17. The process as in claim 12, wherein a gelatin powder having a maximum in the grain size distribution from 20 to 200 μm, preferably ≦50 μm, is employed.

18. The process as in claim 12, wherein the gelatin/pharmaceutical substance mixture is prepared by mixing the gelatin present in sol form with the pharmaceutical substance and then spray-drying.

19. The process as in claim 18, wherein the hydrophilic pharmaceutical substance is dissolved in the aqueous gelatin solution.

20. The process as in claim 18, wherein the lipophilic pharmaceutical substance is dissolved in the gelatin, which is dissolved in an aqueous/organic solvent mixture.

21. The process as in claim 18, wherein the gelatin, which is present dissolved in an aqueous solvent, is emulsified with the liquid or oily pharmaceutical substance at temperatures above 40° C.

22. The process as in claim 18, wherein the very finely divided solid pharmaceutical substance is suspended in the aqueous gelatin solution.

23. The process as in claim 18, wherein the pharmaceutical substance is added to an aqueous or aqueous/organic gelatin solution in colloidal form or produced in the gelatin solution in colloidal form.

24. A sustained release medicament as in claim 1 wherein the matrix consists essentially of gelatin or fractionated gelatin or mixtures thereof.

* * * * *